US009896518B2

(12) United States Patent
Fuchs et al.

(10) Patent No.: US 9,896,518 B2
(45) Date of Patent: Feb. 20, 2018

(54) DILUTE FILTRATION STERILIZATION PROCESS FOR VISCOELASTIC BIOPOLYMERS

(71) Applicant: Bio-Technology General (Israel) Ltd., Rehovot (IL)

(72) Inventors: Menakem Fuchs, Rishon Lezion (IL); Dror Eyal, Nes Ziona (IL); Yehuda Zelig, Nes Ziona (IL)

(73) Assignee: Bio-Technology General (Israel) Ltd., Rehovot (IL)

( * ) Notice: Subject to any disclaimer, the term of this patent is extended or adjusted under 35 U.S.C. 154(b) by 0 days.

(21) Appl. No.: 14/023,196

(22) Filed: Sep. 10, 2013

(65) Prior Publication Data

US 2014/0018315 A1   Jan. 16, 2014

Related U.S. Application Data

(63) Continuation-in-part of application No. 12/742,861, filed as application No. PCT/IB2008/003042 on Nov. 12, 2008, now abandoned.

(30) Foreign Application Priority Data

Nov. 13, 2007 (EP) .................................... 07120568

(51) Int. Cl.
| | |
|---|---|
| *A61K 31/715* | (2006.01) |
| *A61K 47/00* | (2006.01) |
| *C07H 5/06* | (2006.01) |
| *C08B 37/08* | (2006.01) |
| *C08B 37/00* | (2006.01) |
| *C12P 19/26* | (2006.01) |
| *A61K 31/728* | (2006.01) |

(52) U.S. Cl.
CPC ........ *C08B 37/0072* (2013.01); *A61K 31/728* (2013.01); *C08B 37/0003* (2013.01); *C12P 19/26* (2013.01)

(58) Field of Classification Search
USPC ........... 435/101, 885; 514/54, 777; 536/55.1
See application file for complete search history.

(56) References Cited

U.S. PATENT DOCUMENTS

| | | | |
|---|---|---|---|
| 4,141,973 A | 2/1979 | Balazs | |
| 4,517,295 A | 5/1985 | Bracke et al. | |
| 4,713,448 A | 12/1987 | Balazs et al. | |
| 4,780,414 A | 10/1988 | Nimrod et al. | |
| 4,782,046 A | 11/1988 | Brown et al. | |
| 4,784,990 A | 11/1988 | Nimrod et al. | |
| 4,851,521 A | 7/1989 | della et al. | |
| 5,023,175 A | 6/1991 | Hosoya et al. | |
| 5,071,751 A | 12/1991 | Morita et al. | |
| 5,079,236 A | 1/1992 | Drizen et al. | |
| 5,093,487 A | 3/1992 | Brown et al. | |
| 5,099,013 A | 3/1992 | Balazs et al. | |
| 5,316,916 A | 5/1994 | Jones | |
| 5,316,926 A | 5/1994 | Brown et al. | |
| 5,336,767 A | 8/1994 | della et al. | |
| 5,376,537 A * | 12/1994 | Cami et al. .................... | 435/101 |
| 5,411,874 A | 5/1995 | Ellwood et al. | |
| 5,563,051 A | 10/1996 | Ellwood et al. | |
| 6,017,901 A | 1/2000 | Khan et al. | |
| 6,168,719 B1 * | 1/2001 | Shimokawa et al. ......... | 210/652 |
| 6,221,854 B1 | 4/2001 | Radomsky | |
| 6,232,303 B1 | 5/2001 | Callegaro et al. | |
| 6,383,344 B1 | 5/2002 | Miller et al. | |
| 6,489,467 B1 | 12/2002 | Carlino et al. | |
| 6,552,184 B1 | 4/2003 | Pallado et al. | |
| 6,602,693 B1 | 8/2003 | McDonald et al. | |
| 2002/0120132 A1 | 8/2002 | Prescott | |
| 2004/0175387 A1 | 9/2004 | Sood et al. | |
| 2006/0052336 A1 * | 3/2006 | Carlino ........................... | 514/54 |

FOREIGN PATENT DOCUMENTS

| | | |
|---|---|---|
| AU | 198821077 A | 3/1989 |
| EP | 113040 A3 | 7/1984 |
| EP | 216453 A2 | 4/1987 |
| EP | 308279 A1 | 3/1989 |
| FR | 2 785 910 * | 5/2000 |
| GB | 2249315 B | 5/1993 |
| JP | 63094988 U | 6/1988 |
| WO | WO1986004355 A1 | 7/1986 |
| WO | WO1987005517 A1 | 9/1987 |
| WO | WO1992018543 A1 | 10/1992 |
| WO | WO1993013136 A1 | 7/1993 |
| WO | WO1994000134 A1 | 1/1994 |
| WO | WO1995004132 A1 | 2/1995 |
| WO | WO1995024497 A2 | 9/1995 |
| WO | WO1995025751 A1 | 9/1995 |
| WO | WO1998008876 A1 | 3/1998 |
| WO | WO1998045335 A1 | 10/1998 |
| WO | WO1999017821 A1 | 4/1999 |
| WO | WO 2000/039290 | 7/2000 |
| WO | WO2000044925 A1 | 8/2000 |
| WO | WO2001028602 A1 | 4/2001 |
| WO | WO 2004/014399 | 2/2004 |
| WO | WO2009063291 A8 | 9/2009 |

OTHER PUBLICATIONS

Bitter and Muir, "A Modified Uronic Acid Carbazole Reacion", Anal. Biochem., 4:330-334, (1962).

Meyer et al., "The Acid Mucopolysaccharides of Connective Tissue", Biochim Biophys Acta, 21:506-518, (1956).

(Continued)

*Primary Examiner* — Shobha Kantamneni
(74) *Attorney, Agent, or Firm* — Fish & Richardson

(57) ABSTRACT

Manufactured hyaluronic acid products are used in numerous surgical applications including viscoelastic supplementation for the treatment of osteoarthritis, however, traditional sterilization techniques result in the breakdown of such high molecular o weight viscoelastic biopolymers and are thus unsuitable. Disclosed are processes for obtaining concentrated sterile solutions of high molecular weight biopolymers such as hyaluronic acid. The processes include filter sterilization with a dilute preparation of the biopolymer, and concentration of the dilute filter sterilized biopolymer by ultrafiltration to a desired concentration.

19 Claims, No Drawings

(56) References Cited

OTHER PUBLICATIONS

Swann et al., "I. The Preparation and Properties of Rooster Comb Hyaluronic Acid", Biochim Biophys Acta, 156:17-30, (1968).
Yin et al. "Picogram-sensitive assay for endotoxin: Gelation of Limulus polyphemus blood cell lysate induced by purified lipopolysaccharides and lipid A from Gram-negative bacteria", Biocim. biophys. Acta., 261 :284-289, (1972).
International Preliminary Report on Patentability and Written Opinion dated May 18, 2010 for International Appln. No. PCT/IB2008/003042 (6 pgs.).
International Search Report and Written Opinion dated Mar. 25, 2009 for International Appln. No. PCT/IB2008/003042 (10 pgs.).
Remington Pharmaceutical Sciences, The Science and Practice of Pharmacy, Nineteenth Edition, 1995.
Remington Pharmaceutical Sciences, The Science and Practice of Pharmacy, Nineteenth Edition, 1995, pp. 1463-1485.
Akorn, Inc. / Bio-Technology General, (Israel) Ltd., BioLon™ Sodium Hyaluronate Product Information, 4 pp., 1999.
Ferring Pharmaceuticals Inc., Product Information EUFLEXXA®. 2pp., 2011.

* cited by examiner

DILUTE FILTRATION STERILIZATION PROCESS FOR VISCOELASTIC BIOPOLYMERS

CROSS-REFERENCE TO RELATED APPLICATIONS

This application is a continuation-in-part of U.S. application Ser. No. 12/742,861, which was filed on May 13, 2010 as the national phase under 35 U.S.C. 371 of PCT International Appl. PCT/IB2008/003042, filed on Nov. 12, 2008, which claims the benefit of European Patent Appl. 07120568.6, filed Nov. 13, 2007. The subject matter of each of these prior applications is incorporated herein by reference in its entirety.

TECHNICAL FIELD

The present invention relates to a process for formulating a sterile viscoelastic biopolymer such as hyaluronic acid, following bulk manufacture.

BACKGROUND OF THE INVENTION

The invention relates to methods of formulation of viscoelastic biopolymers following bulk manufacture. The biopolymers to which the invention may be applied include homopolysaccharides and heteropolysaccharides, particularly the category of heteropolysaccharides known as glycosaminoglycans. Glycosaminoglycans especially suitable for use in the present invention are hyaluronic acid (HA), chondroitin sulfate, dermatan sulfate, keratan sulfate, heparin and heparan sulfate.

HA is a naturally occurring biopolymer consisting of repeating disaccharide units of D-glucuronic acid in β-(1-3) linkage with N-acetyl-D-glucosamine, wherein each disaccharide unit is connected to its adjoining neighbors by β-(1-4) linkages. The salt sodium hyaluronate (NaHA) is found at physiological pH in human and vertebrate joint synovial fluid, connective tissue, vitreous humor of the eye and healthy skin tissue, and is an extracellular secretion product of several bacterial species, particularly of the genus *Streptococcus*.

To date, the major medical applications of manufactured NaHA products are in ophthalmic surgery for cataracts and intraocular lens implantation, in dermatological applications for filling wrinkles and augmenting lip size, and in viscoelastic supplementation for the treatment of osteoarthritis in humans and large mammals. Viscoelastic supplementation, particularly in the knee, is aimed at restoring the normal rheological homeostasis of the joint network and for providing immediate protection, lubrication, shock absorption, hydrodynamic resistance and a mechanochemical barrier against stress. Intra-articular injections of NaHA have been shown to improve function and mobility and decrease pain.

More recent medical applications of manufactured NaHA include medical device coatings, surgical adhesion prevention products, drug delivery vehicles, bone replacement materials and wound healing materials.

Marketed NaHA products include BioLon™, Biolon™ Prime, BioHy™ (all from Biotechnology General (Israel) Ltd.), Hyalart™ (Fidia), Synvisc™ Hyalan G-F 20 (Biomatrix), Healon™ (Pharmacia), BD Vise™ (Becton Dickinson) and Orthovisc™ (Anika Therapeutics).

For commercial applications in the pharmaceutical, cosmetic and food industries, the quality of a viscoelastic biopolymer is dependent on the combined parameters of viscosity, concentration and molecular weight. For example, HA for pharmaceutical use must be of high molecular weight to ensure sufficient water retention, yet the viscosity must be of reasonable order so as to enable ease of administration and manipulation, e.g., syringeability. NaHA found in biological sources such as rooster combs and culture broths of fermented *Streptococcus* strains, is often of very high molecular weight, i.e., $>3\times10^6$ daltons. Procedures used for its extraction, purification and sterilization typically result however, in a final product in which the molecular weight is significantly reduced as compared to the native compound.

For example, lyophilization of NaHA following repeated extraction induces sublimation of water, the net result of which is shearing of high molecular weight molecules. Low pH techniques result in formation of cross-links, which break upon subsequent pH increase and contribute to shearing of NaHA.

Sterilization techniques, such as those employing dry or moist heat, liquid chemicals, ethylene oxide gas, UV radiation, electron bean radiation, gamma radiation, microwaves and ultrasound all result in breakage of linear molecules, and are thus unsuitable for a viscoelastic biopolymer product in which molecular weight is a key parameter for optimal product quality.

NaHA manufacture from biological sources is well known to those skilled in the art. A typical bulk purification process (of which there are many variations) involves repeated extraction, precipitation, absorption, centrifugation and/or filtration steps to remove contaminants. Procedures for isolation of NaHA from fermented *Streptococcus* cultures are disclosed for example, in U.S. Pat. No. 4,780,414 and U.S. Pat. No. 4,784,990 (both assigned to BioTechnology General (Israel) Ltd.), U.S. Pat. No. 5,563,051, U.S. Pat. No. 5,411,874 (Fermentech Medical), U.S. Pat. No. 5,071,751 (assignee Chisso Corp.) and U.S. Pat. No. 5,316,916.

U.S. Pat. No. 5,023,175 (assignee Kabushiki) relates to purification of cosmetic grade NaHA (MW $2.1\times10^6$) with dialysis ultrafiltration as the final step prior to freeze drying.

U.S. Publication No. 2002/0120132 relates to purification of NaHA (MW>$7.5\times10^5$) involving a temperature controlled reactor and allegedly less ethanol than traditional methods. The purified NaHA is dried under vacuum or lyophilized.

Alternate methods for bulk manufacture of NaHA from Streptococcal cultures avoid extraction/precipitation steps, and rely primarily on sequential filtration techniques as disclosed for example, in GB 2,249,315 (assignee Chisso Corp.), WO 95/04132 (applicant Fidia Corp.) and U.S. Pat. No. 6,489,467 (assignee Chemedica).

None of the above disclose processes for formulating a highly purified bulk manufactured viscoelastic biopolymer such as NaHA into a final sterile product suitable for medicinal use.

U.S. Pat. No. 4,141,973 (assignee Biotrics) discloses a sterile HA produced by extensive purification of material from rooster combs and dissolution of the final product in sterile phosphate buffered saline. The formulation however, has measurable amounts of protein and other impurities.

U.S. Pat. No. 4,517,295 (assignee Diagnostic Inc.) discloses a Streptococcal NaHA product prepared by a process in which sterile-filtration is the terminal step. The disclosed method suffers from the disadvantage of producing low molecular weight NaHA (average MW $5.5\times10^4$ daltons).

U.S. Pat. No. 5,093,487 (assignee Mobay Corp.) and U.S. Pat. No. 5,316,926 (assignee Miles Inc.) disclose final filter-sterilization of a Streptococcal NaHA formulation (average MW $1-2\times10^6$ daltons), following a purification method comprising a mechanical winding technique. The purpose of the winding technique is to increase both molecular weight and viscosity, after which heat treatment or filtration is performed allegedly to reduce viscosity without affecting molecular weight. The winding method is disadvantageous for its unknown effects on the chemical composition of NaHA.

U.S. Pat. No. 4,782,046 (assignee Mobay Corp.) relates to preparing a final NaHA product (average MW generally less than $3.0\times10^6$ daltons) by filter sterilization and/or beta-propiolactone treatment prior to syringe filling. Beta-propiolactone treatment is disadvantageous as traces may remain in the preparation following hydrolization, and it may adversely affect the chemical structure of NaHA.

U.S. Pat. No. 5,079,236 (assignee Hyal Pharmaceutical Corp.) relates to preparing a formulation by dissolving purified NaHA (average MW $5\text{-}20\times10^4$), optionally containing a steroid, in a heated solution of preservatives, e.g., sodium benzoate, methylparaben and propylparaben, adjusting the pH and volume, filling vials and sterilizing the vials in an autoclave. Autoclave sterilization is deleterious to NaHA molecular weight.

U.S. Pat. No. 5,411,874 and U.S. Pat. No. 5,563,051 (assignee Fermentech) relate to preparing a medical grade NaHA solution by dissolving NaHA (average MW $1.6\text{-}2.5\times10^6$) purified by repeated precipitations in sterile phosphate buffered saline.

WO 01/28602 (applicants Genetics Institute and Fidia) relates to injectable formulations comprising HA esters and osteogenic protein.

U.S. Pat. No. 6,221,854 (assignee Orquest) relates to injection formulations comprising NaHA and growth factors.

None of the above disclose industrially applicable methods for formulating bulk manufactured and purified viscoelastic biopolymer such as NaHA into a final product suitable for medicinal use.

An object of the invention is to provide a method for formulating a bulk manufactured and purified viscoelastic biopolymer such as NaHA into a final product suitable for medicinal use.

An object of the invention is to produce a formulation comprising high molecular weight viscoelastic HA that is suitable for administration by injection into ocular and intra-articular spaces in humans and animals.

An object of the invention is to provide an industrial process for formulating NaHA obtained by bulk manufacture into a final product of average molecular weight $3\times10^6$ or greater suitable for medicinal use without subjecting the NaHA to freeze-drying at any stage of manufacture or formulation.

SUMMARY OF THE INVENTION

The invention provides a process for formulating a viscoelastic biopolymer comprising the steps of:
i. sterile-filtering soluble bulk manufactured biopolymer by passage through a membrane suitable for sterile filtration; and
ii. concentrating the biopolymer by ultrafiltration until a desired final concentration is obtained.

The invention also provides a process for formulating a viscoelastic biopolymer comprising the steps of:
i. dissolving bulk manufactured biopolymer in a suitable buffer medium to at least a concentration dilute enough to be suitable for sterile-filtering;
ii. sterile-filtering the biopolymer by passage through a membrane suitable for sterile filtration; and
iii. concentrating the biopolymer by ultrafiltration until a desired final concentration is obtained.

The invention also provides a process for formulating a viscoelastic preparation of hyaluronic acid comprising the steps of:
i. dissolving bulk manufactured hyaluronic acid in a suitable buffer medium to at least a concentration dilute enough to be suitable for sterile-filtering;
ii. sterile-filtering the dissolved hyaluronic acid by passage through a 0.2 micron absolute membrane; and
iii. concentrating the hyaluronic acid by ultrafiltration until a desired final concentration is obtained.

In an additional embodiment the viscoelastic biopolymer is not subjected to freeze drying at any stage of bulk manufacture or formulation.

The invention is suitable for use with glycosaminoglycan biopolymers such as HA. The invention is most suitable for use with viscoelastic biopolymers of high molecular weight, for example HA having a molecular weight in the range of $1\times10^4$ to $1\times10^7$ daltons and having a pseudoplasticity index in the range of 600 to 1200.

The formulations provided by the invention are highly purified, sterile and have favorable rheological properties and are in a form appropriate for injection into ocular and intra-articular spaces in humans and animals.

DETAILED DESCRIPTION OF THE INVENTION

The invention provides a process for formulating a viscoelastic biopolymer comprising the steps of:
i. dissolving bulk manufactured viscoelastic biopolymer in a suitable medium to at least a concentration dilute enough to be suitable for sterile-filtering;
ii. sterile-filtering the dissolved viscoelastic biopolymer by passage through a membrane suitable for sterile filtration; and
iii. concentrating the sterile-filtered viscoelastic biopolymer by ultrafiltration until a desired final concentration is obtained.

The method of the invention is suitable for use with viscoelastic biopolymers for which a highly purified and sterile formulation is required. The viscoelastic biopolymer may be within a wide range of molecular weight, e.g., $1\times10^4$ to $1\times10^7$ daltons, but the method is most particularly suitable for use with viscoelastic biopolymers of high molecular weight since viscosity is a function of both concentration and molecular weight. According to the method of the invention, a bulk manufactured and highly purified viscoelastic biopolymer is sterile-filtered at a relatively low concentration to enable its efficient passage through the filtration apparatus at an applied pressure which does not contribute to biopolymer shearing. As the terminal step in the formulation process prior to package or device filling, the sterile biopolymer is concentrated by ultrafiltration to a desired final concentration.

As used herein the term "high molecular weight" depends on the particular biopolymer to be formulated but generally refers to a molecular weight greater than $1\times10^6$ daltons. A high molecular weight HA viscoelastic biopolymer is generally in the range of $1\times10^6$ to $1\times10^7$ daltons, and more particularly in the range of $2.5\times10^6$ to $5.0\times10^6$ daltons. The method is also applicable to viscoelastic biopolymer preparations in which the molecular weight has been intentionally reduced. For example, reduced molecular weight preparations of HA may be obtained following irradiation treatment, as described in U.S. Pat. No. 6,383,344, or by treatment with ultrasound and sodium hypochlorite as described in U.S. Pat. No. 6,232,303. Other high molecular weights of HA viscoelastic biopolymer useful in the method of the invention may be at least about $1\times10^6$ daltons, at least about $1\times10^7$ daltons, or at least about $1\times10^8$ daltons.

Still other high molecular weight HA viscoelastic biopolymers useful in the method of the invention may be no more than about $2.5\times10^6$ daltons, no more than about $5.0\times10^6$ daltons, no more than about $1\times10^7$ daltons, or no more than about $1\times10^8$ daltons. Alternatively, the high molecular weight HA viscoelastic biopolymers may be about $1\times10^6$ to about $2.5\times10^6$ daltons, about $1\times10^6$ to about $5.0\times10^6$ daltons, about $1\times10^6$ to about $1\times10^7$ daltons, about $1\times10^6$ to about $1\times10^8$ daltons, about $2.5\times10^6$ to about $5.0\times10^6$ daltons, about $2.5\times10^6$ to about $1\times10^7$ daltons, about $2.5\times10^6$ to about $1\times10^8$ daltons, about $5.0\times10^6$ to about $1\times10^7$ daltons, about $5.0\times10^6$ to about $1\times10^8$ daltons, or about $1\times10^7$ to about $1\times10^8$ daltons.

The viscoelastic biopolymer suitable for the method of the invention may be a homopolysaccharide, i.e., assembled from a single type of monosaccharide, or a heteropolysaccharide, i.e., assembled from two or more different types of monosaccharides. Examples of homopolysaccharides include carboxymethylcellulose, chitin, polymannuronic acid, curdlan gum, scleroglucan and dextran. Examples of heteropolysaccharides include glycosaminoglycans, alginates, carageenans, guar gum, pectins, locust bean gum and xanthum gum. The method of the invention is particularly suitable for glycosaminoglycans, also known as acid mucopolysaccharides, which are composed of repeating disaccharide units in which one of the two monosaccharides is always either N-acetylglucosamine or N-acetylgalactosamine. Examples of glycosaminoglycans include HA, chondroitin, chondroitin sulfate A, chondroitin sulfate B, chondroitin sulfate C, dermatan sulfate, keratan sulfate, heparin and heparan sulfate. Both homo- and heteropolysaccharides may be linear or branched structures. The component monosaccharides of a biopolymer may be released by acid hydrolysis and detected by analytical techniques such as thin layer chromatography and/or high pressure liquid chromatography.

The viscoelastic biopolymer should be soluble in aqueous solution. Those which are soluble and liquid at temperatures in the range of 10-30° C. are most suitable for the method of the invention, but those which are soluble only at elevated temperatures e.g., locust bean gum may also be formulated using the method of the invention. A viscoelastic biopolymer which is normally insoluble in aqueous solution may be rendered suitable for the method of the invention upon derivatization by chemical treatment. For example, while cellulose is insoluble, the derivative carboxymethylcellulose formed by reaction of cellulose with alkali and chloroacetic acid, is soluble and may be formulated using the method of the invention.

According to the invention, the biopolymer may be in its native form or it may be chemically modified and/or derivatized. Examples of chemical modification/derivatization include cross-linking (U.S. Pat. No. 6,552,184), addition of sulfate (WO 95/25751; WO 98/45335), carboxyl or hydroxyl groups, attachment of lipophilic side chains, introduction of acetyl groups, and esterification with and without additional moieties attached (EP Pat. No. 216,453; WO 98/08876). Additional moieties include drugs, polysaccharides, lectins, imaging agents, targeting proteins such as antibodies, growth factors, and the like.

The native form of a biopolymer may an anionic, cationic or neutral salt form.

The method of the invention is particularly suitable for HA. The term hyaluronic acid (HA) means hyaluronic acid, salts thereof, such as sodium, potassium, magnesium, calcium, lysine, ammonium, triethanolamine and propanolamine hyaluronates, metal salts thereof, such as cobalt, zinc, copper, iron, manganese and lithium hyaluronate, and chemically modified and derivatized forms thereof, as disclosed for example in U.S. Pat. No. 4,851,521, U.S. Pat. No. 5,099,013, U.S. Pat. No. 5,336,767, and U.S. Pat. No. 6,017,901.

As used herein, the term viscoelastic refers to the rheological behavior of a biopolymer solution, which under the effect of shear displays both the characteristics of a purely elastic material, i.e., capable of storing energy, and the characteristics of a purely viscous material, i.e., capable of dissipating energy.

Rheological behavior is characteristic and specific and is a function of the biopolymer's length, structure and charge. Some biopolymers, such as HA, display non-Newtonian behavior, indicating that the viscosity is dependent on both shear rate and temperature, and they display pseudoplastic behavior (also known as "shear-thinning"), which means that the solution viscosity decreases as a function of increasing shear force.

Viscosity of a particular biopolymer is quantified at a set of discrete shear rates and temperatures, e.g., using a Brookfield viscometer. Further information may be obtained over a continuous range of shear, e.g., using a Haake rotational viscometer.

Viscoelasticity may be quantitated as the ratio of the viscosity at a low shear rate, e.g., 0.1 $sec^{-1}$, to the viscosity at a high shear rate, e.g., 1000 $sec^{-1}$. As used herein, viscoelasticity refers to the ratio of measured viscosity at an applied shear rate of 0.1 $sec^{-1}$ to the measured viscosity at an applied shear rate of 1000 $sec^{-1}$. This ratio is also known as the pseudoplasticity index (PI):

PI=viscosity at shear rate 0.1 $sec^{-1}$/viscosity at shear rate 1000 $sec^{-1}$ As used herein, a viscoelastic biopolymer has a pseudoplasticity index greater than about 500. The PI is a useful index for characterizing the behavior of a biopolymer under different conditions, and for comparing rheological quality among different biopolymer solutions.

A biopolymer such as HA which is used for viscoelastic supplementation and is administered by intra-articular injection, requires high viscosity at low shear rates, so that it can serve as a non-flowing support following injection, but it also requires low viscosity at high shear rate, i.e., while it is being delivered, e.g., by injection (e.g., through a syringe and needle), so that the delivery can be reasonable effortless and accurate. Hence the PI of a biopolymer solution directly influences its syringeability.

Syringeability is the force required to expel a biopolymer solution from a syringe or a syringe-like application device. Syringeability may be tested using a Force indicator e.g., Mecmesin Force Indicator, and is expressed in units of g (gravity). For example, a force of 200 g allows a medical practitioner to efficiently expel NaHA solution from a syringe and simultaneously control the amount of material introduced to the desired location, e.g., an intra-articular or ocular space.

According to the invention, the biopolymer may be obtained from a biological source, or it may be a product of in vitro enzymatic or chemical synthesis, or combinations thereof. A biological source may be a bacterial, yeast, plant, amphibian, avian or mammalian organism. For example, HA may be isolated from any of fermented Streptococcal cultures, human umbilical cords, bovine cartilage or rooster combs. In vitro enzymatic synthesis of polysaccharides, including HA, cellulose, polymannuronic acid and chitin is described in WO 95/24497. The use of a recombinantly-produced hyaluronan synthase enzyme for in vitro synthesis of HA is described in U.S. Pat. No. 6,602,693. HA obtained from any of the aforementioned sources may be subsequently chemically modified or derivatized as described, for example, in U.S. Pat. No. 4,851,521, U.S. Pat. No. 4,713,448, U.S. Pat. No. 5,336,767 and U.S. Pat. No. 5,099,013.

Additional viscoelastic biopolymers which are the products of bacterial fermentation include, for example, curdlan gum (β-1-3-D-glucan), produced by *Alcaligenes faecalis*, gellan gum (tetrasaccharide backbone of L-rhamnose and D-glucose with glyceryl and acetyl substituents) produced by *Sphingomonas elodea* and xanthum gum (β-1-4-D-glucan with mannose and glucuronic acid side chains), produced by *Xanthomonas campedis*.

In the field of HA manufacturing, the upstream process of bulk purification has many variations which are well known to those skilled in the art. Processes for bulk manufacturing of a solution containing high molecular weight HA from fermented *Streptococcus* cultures are disclosed, for example, in U.S. Pat. No. 5,563,051 and U.S. Pat. No. 5,316,916. Other bulk manufacturing processes have been described which yield solid forms of HA as a final product, as described in U.S. Pat. No. 4,780,414.

The downstream process of formulation, however, is less variable, in that the usual practice is to sequentially perform concentration and sterilization as the final sequence of operations prior to package or device filling. Indeed, according to usual best practice in the biopharmaceutical industry, sterilization is the final step prior to filling, and intermediate steps are specifically avoided to minimize the potential for contamination.

In the process of the invention, the usual industrial practice is unexpectedly avoided and indeed reversed, in that sterilization (by filtration through an absolute filter of pore size 0.22 micron or less) is carried out prior to concentration (by ultrafiltration). The concentration step is carried out aseptically and the final product may be expected to be of pharmaceutical grade of the highest standard without any compromise in sterility, or other quality parameters. Indeed, it is unexpected that an HA product of high molecular weight and viscosity can be formulated on a large aseptic scale where the concentration step is carried out as an intermediate step between sterile filtering and filling.

This unexpected order of operations is highly advantageous when applied to a high molecular weight viscoelastic biopolymer such as HA. One such significant aspect is that the bulk manufactured and dissolved HA (e.g., 0.1%; 1 mg/mL) easily passes through the sterile filter at an industrially applicable level of pressure to achieve an acceptable flow rate (e.g., minimum flow rate 750 mL/min). The pressure exerted to drive the HA solution through the sterile filter is sufficiently mild so as to not adversely affect the molecular weight of the HA.

The reverse process of concentrating e.g., to 1% or 10 mg/mL, followed by terminal sterilization is, in practice, unworkable with a high molecular weight viscoelastic biopolymer, since the high biopolymer concentration results in repeated blockage of the sterilizing filter apparatus, resulting in an ultimately inefficient and wasteful procedure.

Furthermore, using the method of the invention, the bulk manufactured and filter-sterilized HA is a flexible intermediate product in that it may be brought to different final concentrations and/or mixed with additional sterile excipients or active ingredients for different final formulations.

According to the method of the invention, sterilization of the viscoelastic biopolymer must be carried out by filtration through an appropriate membrane in order to retain the high molecular weight structure of the polymer. Alternate sterilization techniques, such as those employing dry or moist heat, liquid chemicals, ethylene oxide gas, UV radiation, electron bean radiation, gamma radiation, microwaves or ultrasound result in breakage of long linear molecules, such as those of HA.

A preferable bulk manufacturing process suitable for the invention is one which consistently yields a viscoelastic biopolymer product which is homogeneous on a batch to batch basis with respect to a wide range of physicochemical and purity parameters. The bulk manufacturing process is essentially a purification process which must be sufficiently rigorous so as to remove minute quantities of impurities originating from the production source (e.g., bacterial culture) and from the extraction reagents (e.g., ethanol or cetylpyridinium chloride), all of which can cause adverse reactions if administered to patients. For a product such as HA intended for injection into patients, the manufacture, specifications and characterization of the bulk manufactured HA should be in accordance with internationally recognized standards and guidelines for the evaluation of toxicity, endotoxin levels and sterility.

On the other hand, the bulk manufacturing process should not comprise steps which result in excessive shearing of the HA molecule and concomitantly reduce its molecular weight, e.g., to less than about $3 \times 10^6$ daltons, or viscosity, or otherwise result in deviations from the characteristic properties of the HA molecule.

A suitable bulk manufacturing process is disclosed for example in U.S. Pat. No. 4,780,414. Such a process comprises the following steps:

i. precipitating with ethanol a culture broth of a non-hemolytic nonpathogenic hyaluronic acid-producing fermented *Streptococcus* strain;

ii. dissolving the precipitate obtained in step (i) in sodium chloride/ethanol/charcoal;

iii. precipitating the dissolved material obtained in step (ii) with cetylpyridinium chloride;

iv. dissolving the precipitate obtained in step (iii) in sodium chloride/ethanol;

v. treating the dissolved material obtained in step (iv) with magnesium silicate;

vi. filtering the treated material obtained in step (v) through a 0.65 micron absolute membrane; and vii. precipitating the filtrate obtained in step (vi) with ethanol.

Bulk manufacture and formulation should be carried out only on culture broth batches in which the molecular weight of HA exceeds a desired value for high molecular weight HA, e.g., 3.0±0.6 megadaltons. The molecular weight can be in the range from about 2.8 megadaltons to about 3.2 megadaltons.

Preferably, the bulk manufacturing process should yield a product in which the bioburden is zero or substantially close to zero. Preferably the zero or substantially close to zero bioburden should be achieved about half way through the bulk manufacturing process e.g., from the second dissolution step of the above-mentioned process. The precipitated HA is preferably stored under ethanol, and then vacuum dried and stored at 4° C. in sterile containers to protect the bulk manufactured HA against contamination prior to the formulation process.

The bulk manufactured HA should be characterized by assessment of purity, molecular weight, viscosity, pH, specific rotation, concentration, % HA content and any other necessary parameters in order to verify batch to batch consistency and quality and thereby assess the efficiency and suitability of the bulk manufacturing process. Preferably the purity of the bulk manufactured HA is such that the endotoxin content is <0.25 EU/mL, and more preferably <0.10 EU/mL, and the protein content is <1 mg/g, absorbance at 257 nm of a 1% solution is <0.20, the oxidative burst absorbance at 550 nm is <0.10 and the viable count of aerobic bacteria is <4 CFU/g. Preferably the quality of the bulk manufactured HA is such that the pH is from 6.0-8.0, the specific rotation is from −72.8°-90.8°, the limiting viscosity number is 2680-3410 mL/g, and the molecular weight is $2.4-3.6 \times 10^6$ daltons.

Since HA does not significantly absorb at wavelengths above 240 nm, any significant absorbance in the 240-300 nm range is attributable to organic contaminants such as proteins and nucleic acids. Absorbance at 257 nm indicates contamination with nucleotides, DNA or RNA while absorbance at 280 nm indicates contamination with proteins or amino acids. Absorbance at 257 nm below certain limits, e.g., 0.2, is conveniently used as an indication of HA purity. Measured absorbance which is substantially close to zero, e.g., <0.08, indicates absolute purity.

Purity assessment additionally involves analysis for purification reagents, e.g., ethanol, detergent, used in the bulk manufacturing process. Such analyses are conveniently carried out by HPLC and should indicate the substantial absence of reagents.

Bacterial endotoxin (lipopolysaccharide) may be quantitated, for example, by using the kinetic turbidimetric Limulus Amebocyte Lysate (LAL) assay (see Yin et al. (1972), *Biochim. Biophvs. Acta*. 261:284-289).

Inflammatory material may be assessed using a mouse peritoneal exudate cell assay which quantitates oxidative burst activity following intraperitoneal injection of test material, e.g., as described in U.S. Pat. No. 4,780,414.

The measured specific rotation relates to the characteristic concentration-dependent light polarization of HA in solution. At a given concentration, the degree of polarization at a specific wavelength is an inherent property of the molecule, characterized by its specific rotation constant [α], values of which are known from the scientific literature (Meyer et al. (1956) *Biochim. Biophvs. Acta* 21:506-518; Swann et al. (1968) *Biochim. Biophvs. Acta* 156:7-30).

Thus, HA concentration (c) may be estimated using the equation:

$$c = R \times \frac{1000}{[\alpha]}$$

where R=polarimeter reading in degrees, and c=concentration (g/L).

HA concentration can also be estimated by the colorimetric carbazole assay (Bitter and Muir (1962) *Anal. Biochem.* 4:330-334), which is based on the reaction of the carbazole reagent with the HA glucuronate residues released upon exhaustive hydrolysis.

The molecular weight of the bulk manufactured HA is determined using the limiting viscosity number or intrinsic viscosity (expressed in volume per mass) obtained from viscometry measurements, and the empirically established Mark-Houwink equation, as described in Example I and in U.S. Pat. No. 4,780,414.

Absolute measurements of the HA molecular weight may be obtained using the low-angle laser light scattering (LALLS) method as is known in the art.

Viscosity of a biopolymer solution may be measured at discrete shear rates, e.g., using a Brookfield LVTD viscometer, as well as over a continuous range of shear rates, e.g., using a Haake rotational viscometer.

Upon determination that a bulk manufactured HA batch is of sufficient purity, concentration, viscosity and molecular weight, the formulation process according to the method of the invention may be initiated, and all steps are preferably conducted under clean room conditions. The bulk manufactured HA is most conveniently in solid form i.e., following precipitation and vacuum drying, so that using the process of the invention it may be formulated in the desired medium, e.g., buffer and excipients.

Preferably, the biopolymer is not subjected to freeze drying at any stage of bulk manufacturing or formulation.

An appropriate amount of bulk manufactured HA is dissolved in a suitable medium to achieve a suitable concentration enabling sterile-filtering.

A suitable medium for biopolymer dissolution includes the buffer and/or primary excipient found in the final formulation. For biopolymer formulations intended for injection, such a buffer or excipient should preferably be physiologically acceptable. Suitable media include sodium chloride, phosphate buffered saline, and buffers containing citrate, bicarbonate, acetate and benzylalkonium salts, including metal salts. The dissolution medium may further comprise additional excipients present in the final formulation such as chelating agents, isotonicity agents, antimicrobial agents, antiviral agents, preservatives and surfactants. The dissolution medium may further comprise additional pharmaceutically active agents such as antibiotics, antimicrobial agents, antiviral agents, steroids, non-steroidal anti-inflammatory drugs, glucocorticoids, growth factors, prostaglandins, vitamins, enzymes, enzyme inhibitors, antioxidants, antihistamines, prodrugs, anaesthetic agents, analgesic agents, antihypertensive agents and antiangiogenic agents.

For biopolymer dissolution, an appropriate vessel is filled with water for injection (WFI) (70-80% of final volume) having a temperature of 4-50° C. The appropriate amounts of medium reagents (dry or liquid) are added and stirred, following which an appropriate amount of bulk manufactured biopolymer is added. WFI is added to the appropriate final volume to achieve a solution in which the biopolymer concentration permits subsequent sterile filtration. Stirring process is carried out until complete dissolution of the biopolymer is achieved, typically 10-36 hours for HA.

Optionally, excipients may be added towards the end of the stirring period, for example to avoid excess foaming of surfactants.

An appropriate vessel for dissolution is fitted with a mixing apparatus such as a double spiral and has an industrial scale volume capacity. The vessel should be closed to protect the biopolymer from natural and artificial illumination, thereby avoiding photo flux effects. Similarly, the material of the dissolution vessel should be inert towards the biopolymer.

The concentration achieved by the dissolution process should be one that enables sterile-filtration at an industrially acceptable flow rate (e.g., 750 mL/min) using an exerted pressure {e.g., 10-15 psi) which does not adversely affect the molecular weight of the biopolymer.

For HA of molecular weight about $3 \times 10^6$ daltons, an appropriate concentration following dissolution is 0.1-0.13%; 1.0-1.3 mg/mL.

According to the method of the invention, biopolymer dissolution is followed by sterile filtration using an appropriate filter housed in a sterilization unit. Preferably the dissolution vessel and the sterilization unit are physically connected by an appropriate tubing and valve system which is removable, modular and sterilizable. The dissolution and sterilization units may be located in separate rooms with the connecting tubing and valve system being positioned through the wall separating the rooms. The sterilization unit should be fitted with means to perform sterilization in place (SIP) and cleaning in place (CIP) of relevant components such as inlet and outlet valves.

The filter in the sterilization unit should have an absolute pore size of 0.05-0.2 μm and should be validated for bacterial and viral particle retention using appropriate challenge regimens. The filter is also preferably graded for endotoxin particle retention. The filter may be hydrophilic or hydrophobic and should be selected on the basis of the hydrophobicity and charge of the biopolymer. Materials used for sterilizing filters include, but are not limited to, polyethersulfone (PES), polyvinylidene fluoride (PVDF), polytetrafluorethylene (PTFE), polypropylene, polyethylene, polyamide, cellulose, cellulose acetate, cellulose mixed esters or other cellulose derivatives and nylon. Manufacturers of suitable sterilization filters include but are not limited to Millipore, Meissner, Sartorius, and the like.

The filter is preferably housed in a cartridge designed for industrial purposes. Such cartridges are usually supplied in various lengths, most commonly 10, 20 and 30 inches, and accordingly provide differing filtration surface areas. For example, a 30 inch Durapore™ 0.2 μm (Millipore) filter cartridge provides a surface area of 20,700 cm$^2$.

In a typical sterilization process of a solution of 0.1% NaHA, a hydrophilic 0.2 μm filter cartridge 30 inches in length, for example Durapore™ (Millipore) or Sartobran™ (Sartorius) is used. Filtration is performed under 10-15 psi, and back pressure of 1.5-2 bar is applied after each 15-20 L of solution. A minimal flow rate of about 750 mL/min should be maintained. The filters should be subjected to bubble point and diffusion testing before and after each use. The filters may be reused following cleaning and sterilization according to the manufacturer's recommendation and validation of the sterilizing properties of the re-used filters.

The sterile filtered biopolymer is fed into a concentration unit which is connected to the sterilization unit via an appropriate tubing and valve system. All inlet and outlet points of the concentration unit should be fitted with means to perform SIP and CIP of relevant components.

The concentration unit is fitted with an ultrafiltration membrane. The ultrafiltration membrane may be a ceramic, polysulfone, polyethersulfone, cellulose acetate, hydrolyzed PES or PVDF or stainless steel membrane. The ultrafiltration membrane may be of plate and frame, hollow fiber or spiral wound construction. A suitable ceramic membrane may be composed of titanium oxide, zirconium oxide, aluminum oxide, silicon oxide or mixtures thereof. The ultrafiltration membrane should have a pore size of 0.002 to 0.1 μm; and a pore size of 50 nm is preferable for HA.

Concentration by ultrafiltration is continued until the desired final concentration of the biopolymer is achieved. For example, a desired final concentration for NaHA is 1.0-2.0%; 10-20 g/L. The desired final concentration can be in the range from 0.8 to 3.0% w/v. The desired final concentration can be about 1.0% w/v. The desired final concentration can be about 1.2% w/v. The desired final concentration can be about 2.0% w/v. The desired final concentration can be in the range from 0.9 to 1.3% w/v.

The efficiency of the ultrafiltration process may be assessed by determining the concentrations of the biopolymer in the retentate as compared to the ultrafiltrate. A minimal concentration in the ultrafiltrate, e.g., less than 1% compared to that in the retentate, indicates an acceptable level of efficiency.

Following concentration to the desired concentration, the biopolymer solution may be optionally transferred to an intermediate tank in which degassing and stirring are performed to ensure uniformity of the product.

The final formulated biopolymer product is then transferred to a suitable automated filling machine in which uniform aliquots, e.g., 0.5 mL, 1.0 mL or 2.0 mL are used to fill units of a suitable sterile package or delivery device such as a vial, syringe, catheter or nebulizer.

The formulated biopolymer should be assessed for key quality parameters, particularly molecular weight, concentration, viscosity, osmolality, purity, endotoxin content, absorbance, pH and bioburden, as is carried out for assessment of the bulk manufactured biopolymer. Additional parameters associated with the final formulated product, such as syringeability and package integrity are also assessed.

In some embodiments, the formulated biopolymer, e.g., hyaluronic acid, may further comprise additional pharmaceutically active agents such as antibiotics, antimicrobial agents, antiviral agents, steroids, non-steroidal anti-inflammatory drugs, glucocorticoids, growth factors, prostaglandins, vitamins, enzymes, enzyme inhibitors, antioxidants, antihistamines, prodrugs, anaesthetic agents, analgesic agents, antihypertensive agents and antiangiogenic agents. The formulated biopolymer, e.g., hyaluronic acid, may also include additional compounds for improving joint lubrication such as a microalgal polysaccharide such as a polysaccharide isolated from a microalga of the genus *Porphyridium*. Including a polysaccharide isolated from a microalga of the genus *Porphyridium* in a hyaluronic acid-containing formulation can provide longer half-life to the formulated hyaluronic acid due to potent inhibition of hyaluronidase by polysaccharides isolated from microalgae of the genus *Porphyridium*.

Thus, the present application provides:

¶1. A process for formulating a soluble viscoelastic biopolymer comprising:
(i) sterile-filtering soluble bulk manufactured biopolymer by passage through a membrane suitable for sterile filtration; and
(ii) concentrating the biopolymer by ultrafiltration to a desired final concentration.

¶2. The process as described in ¶1, wherein the biopolymer is selected from the group consisting of a homopolysaccharide, a heteropolysaccharide and mixtures thereof.

¶3. The process as described in ¶2, wherein the homopolysaccharide is selected from the group consisting of carboxymethylcellulose, chitin, polymannuronic acid, curdlan gum and dextran.

¶4. The process as described in ¶2, wherein the heteropolysaccharide is selected from the group consisting of hyaluronic acid, chondroitin sulfate, dermatan sulfate, keratan sulfate, heparin, heparan sulfate, agar, alginate, carrageenan, gellan, guar gum, locust bean gum, and xanthan gum.

¶5. The process as described in ¶1, wherein the biopolymer is obtained from a source selected from the group consisting of a biological source, an in vitro enzymatic synthesis, a chemical synthesis, and combinations of two or more such sources.

¶6. The process as described in ¶5, wherein the biological source is selected from the group consisting of a bacterium, a yeast, a plant, an amphibian, an avian and a mammal.

¶7. The process as described in ¶5, wherein the biopolymer obtained from a biological source further comprises a chemical modification.

¶8. The process as described in ¶7, wherein the chemical modification comprises a modification selected from the group consisting of addition of sulfate groups, addition of carboxyl groups, addition of hydroxyl groups, addition of acetyl groups, esterification and cross-linking.

¶9. The process as described in ¶1, wherein the viscoelastic biopolymer has an average molecular weight in the range from $1\times10^4$ to $1\times10^7$ daltons.

¶10. The process as described in ¶9, wherein the viscoelastic biopolymer has an average molecular weight of $3\times10^6 \pm 0.6\times10^6$ daltons.

¶11. The process as described in ¶9, wherein the viscoelastic biopolymer has an average molecular weight in the range from $2.8\times10^6$ to $3.2\times10^6$ daltons.

¶12. The process as described in ¶6, wherein the bacterium is a strain of the genus *Streptococcus*.

¶13. The process as described in ¶12, wherein the bacterium is a *Streptococcus* species selected from the group consisting of *Streptococcus equi, Streptococcus pyogenes, Streptococcus equisimilis, Streptococcus dysgalactiae* and *Streptococcus zooepidemicus*.

¶14. The process as described in ¶12, wherein the *Streptococcus* strain is non-hemolytic and non-pathogenic.

¶15. The process as described in ¶1, wherein the bulk manufactured biopolymer is isolated from a culture broth of a fermented *Streptococcus* strain.

¶16. The process as described in ¶15, wherein the bulk manufactured biopolymer is hyaluronic acid.

¶17. The process as described in ¶16, wherein the bulk manufactured hyaluronic acid is substantially free of impurities.

¶18. The process as described in ¶17, wherein the bulk manufactured hyaluronic acid is substantially free of bacterial endotoxin.

¶19. The process as described in ¶18, wherein the level of bacterial endotoxin is <0.25 EU/mL.

¶20. The process as described in ¶17, wherein the bulk manufactured hyaluronic acid is substantially free of bacterial cells.

¶21. The process as described in ¶20, wherein the viable count of bacterial cells is <100 CFU/g.

¶22. The process as described in ¶21, wherein the viable count of bacterial cells is <50 CFU/g.

¶23. The process as described in ¶22, wherein the viable count of bacterial cells is <10 CFU/g.

¶24. The process as described in ¶17, wherein the bulk manufactured hyaluronic acid is substantially free of protein.

¶25. The process as described in ¶24, wherein the level of protein is <1 mg/g.

¶26. The process as described in ¶1, wherein the concentration of the soluble bulk manufactured biopolymer in step (i) is <0.2%.

¶27. The process as described in ¶26, wherein the concentration of the soluble bulk manufactured biopolymer in step (i) is 0.10-0.13%.

¶28. The process as described in ¶1, wherein the concentrating is carried out by ultrafiltration.

¶29. The process as described in ¶28, wherein the ultrafiltration is carried out using a ceramic membrane.

¶30. The process as described in ¶1, wherein the desired final concentration in step (ii) is in the range of 0.8 to 3.0% w/v.

¶31. A process as described in ¶30, wherein the desired final concentration is about 1.0% w/v.

¶32. A process as described in ¶30, wherein the desired final concentration is about 1.2% w/v.

¶33. A process as described in ¶30, wherein the desired final concentration is about 2.0% w/v.

¶34. A process as described in ¶30, wherein the desired final concentration in step (ii) is in the range from 0.9 to 1.3% w/v.

¶35. A process as described in ¶1, further comprising aseptic filling of a suitable packaging device with the biopolymer.

¶36. A process as described in ¶35, wherein the packaging device is selected from the group consisting of a syringe, a vial, a catheter and a nebulizer.

¶37. A process as described in ¶1, wherein the formulated viscoelastic biopolymer has a pseudoplasticity index in the range from 500 to 4000.

¶38. A process as described in ¶37, wherein the pseudoplasticity index is in the range from 600 to 1200.

¶39. A process as described in ¶38, wherein the pseudoplasticity index is in the range from 600 to 800.

¶40. A process as described in ¶1, wherein the sterile-filtering is carried out using a membrane of absolute pore size 0.2 micron.

¶41. A process for formulating a viscoelastic biopolymer comprising:
(i) dissolving bulk manufactured biopolymer in a suitable buffer medium to achieve a dilute concentration for sterile-filtering;
(ii) sterile-filtering the biopolymer by passage through a membrane suitable for sterile filtration; and
(iii) concentrating the biopolymer by ultrafiltration to a desired final concentration.

¶42. The process as described in ¶41, wherein the biopolymer is selected from the group consisting of a homopolysaccharide, a heteropolysaccharide and mixtures thereof.

¶43. The process as described in ¶42, wherein the homopolysaccharide is selected from the group consisting of carboxymethylcellulose, chitin, polymannuronic acid, curdlan gum and dextran.

¶44. The process as described in ¶42, wherein the heteropolysaccharide is selected from the group consisting of hyaluronic acid, chondroitin sulfate, dermatan sulfate, keratan sulfate, heparin, heparan sulfate, agar, alginate, carrageenan, gellan, guar gum, locust bean gum, and xanthan gum.

¶45. The process as described in ¶41, wherein the biopolymer is obtained from a source selected from the group consisting of a biological source, an in vitro enzymatic synthesis, a chemical synthesis, and combinations of two or more such sources.

¶46. The process as described in ¶45, wherein the biological source is selected from the group consisting of a bacterium, a plant, an amphibian, an avian and a mammal.

¶47. The process as described in ¶45, wherein the biopolymer obtained from a biological source further comprises a chemical modification.

¶48. The process as described in ¶47, wherein the chemical modification comprises a modification selected from the group consisting of addition of sulfate groups, addition of carboxyl groups, addition of hydroxyl groups, addition of acetyl groups, esterification, and cross-linking.

¶49. The process as described in ¶41, wherein the viscoelastic biopolymer has an average molecular weight in the range from $1\times10^4$ to $1\times10^7$ daltons.

¶50. The process as described in ¶49, wherein the viscoelastic biopolymer has an average molecular weight of $3\times10^6\pm0.6\times10^6$ daltons.

¶51. The process as described in ¶49, wherein the viscoelastic biopolymer has an average molecular weight in the range from $2.8\times10^6$ to $3.2\times10^6$ daltons.

¶52. The process as described in ¶46, wherein the bacterium is a strain of the genus *Streptococcus*.

¶53. The process as described in ¶52, wherein the bacterium is a *Streptococcus* species selected from the group consisting of *Streptococcus equi*, *Streptococcus pyogenes*, *Streptococcus equisimilis*, *Streptococcus dysgalactiae* and *Streptococcus zooepidemicus*.

¶54. The process as described in ¶52, wherein the *Streptococcus* strain is nonhemolytic and non-pathogenic.

¶55. The process as described in ¶41, wherein the bulk manufactured biopolymer is isolated from a culture broth of a fermented *Streptococcus* strain.

¶56. The process as described in ¶55, wherein the bulk manufactured biopolymer is hyaluronic acid.

¶57. The process as described in ¶56, wherein the bulk manufactured hyaluronic acid is substantially free of impurities.

¶58. The process as described in ¶57, wherein the bulk manufactured hyaluronic acid is substantially free of bacterial endotoxin.

¶59. The process as described in ¶58, wherein the level of bacterial endotoxin is <0.25 EU/mL.

¶60. The process as described in ¶56, wherein the bulk manufactured hyaluronic acid is substantially free of bacterial cells.

¶61. The process as described in ¶60, wherein the viable count of bacterial cells is <100 CFU/g.

¶62. The process as described in ¶61, wherein the viable count of bacterial cells is <50 CFU/g.

¶63. The process as described in ¶62, wherein the viable count of bacterial cells is <10 CFU/g.

¶64. The process as described in ¶57, wherein the bulk manufactured hyaluronic acid is substantially free of protein.

¶65. The process as described in ¶64, wherein the level of protein is <1 mg/g.

¶66. The process as described in ¶41, wherein the dissolving in step (i) yields soluble bulk manufactured biopolymer at a concentration of <0.2%.

¶67. The process as described in ¶66, wherein the dissolving in step (i) yields soluble bulk manufactured biopolymer at a concentration is in the range of 0.10-0.13%.

¶68. The process as described in ¶41, wherein the concentrating in step (ii) is carried out by ultrafiltration.

¶69. The process as described in ¶68, wherein the ultrafiltration is carried out using a ceramic membrane.

¶70. The process as described in ¶41, wherein the desired final concentration in step (iii) is in the range of 0.8 to 3.0% w/v.

¶71. A process as described in ¶70, wherein the desired final concentration is about 1.0% w/v.

¶72. A process as described in ¶70, wherein the desired final concentration is about 1.2% w/v.

¶73. The process as described in ¶70, wherein the desired final concentration is about 2.0% w/v.

¶74. A process as described in ¶41, wherein the desired final concentration in step (iii) is in the range from 0.9 to 1.3% w/v.

¶75. The process as described in ¶41, further comprising aseptic filling of a suitable packaging device with the biopolymer.

¶76. The process as described in ¶75, wherein the packaging device is selected from the group consisting of a syringe, a vial, a catheter and a nebulizer.

¶77. The process as described in ¶41, wherein the formulated viscoelastic biopolymer has a pseudoplasticity index in the range from 500 to 4000.

¶78. The process as described in ¶77, wherein the pseudoplasticity index is in the range from 600 to 1200.

¶79. The process as described in ¶78, wherein the pseudoplasticity index is in the range from 600 to 800.

¶80. The process as described in ¶41, wherein the sterile-filtering is carried out using a membrane of absolute pore size 0.2 micron.

¶81. The process as described in ¶41, wherein the buffer medium comprises a metal salt.

¶82. A process for formulating a viscoelastic preparation of hyaluronic acid comprising:
  (i) dissolving bulk manufactured hyaluronic acid in a suitable buffer medium to achieve a dilute concentration for sterile-filtering;
  (ii) sterile-filtering the dissolved hyaluronic acid by passage through a 0.2 micron absolute membrane; and
  (iii) concentrating the hyaluronic acid by ultrafiltration to a desired final concentration.

¶83. The process as described in ¶82, wherein the bulk manufactured hyaluronic acid is obtained from a source selected from the group consisting of a biological source, an in vitro enzymatic synthesis, a chemical synthesis, and combinations of two or more such sources.

¶84. The process as described in ¶83, wherein the biological source is selected from the group consisting of a bacterium, a yeast, a plant, an amphibian, an avian and a mammal.

¶85. The process as described in ¶84, wherein the bulk manufactured hyaluronic acid obtained from a biological source further comprises a chemical modification.

¶86. The process as described in ¶85, wherein the chemical modification comprises a modification selected from the group consisting of addition of sulfate groups, addition of carboxyl groups, addition of hydroxyl groups, addition of acetyl groups, esterification, and cross-linking.

¶87. The process as described in ¶82, wherein the bulk manufactured hyaluronic acid has an average molecular weight in the range from $1\times10^4$ to $1\times10^7$ daltons.

¶88. The process as described in ¶87, wherein the bulk manufactured hyaluronic acid has an average molecular weight of $3\times10^6\pm0.6\times10^6$ daltons.

¶89. The process as described in ¶87, wherein the bulk manufactured hyaluronic acid has an average molecular weight in the range from $2.8\times10^6$ to $3.2\times10^6$ daltons.

¶90. The process as described in ¶84, wherein the bacterium is a species of the genus *Streptococcus*.

¶91. The process as described in ¶90, wherein the bacterium is a *Streptococcus* species selected from the group consisting of *Streptococcus equi*, *Streptococcus pyogenes*, *Streptococcus equisimilis*, *Streptococcus dysgalactiae* and *Streptococcus zooepidemicus*.

¶92. The process as described in ¶90, wherein the *Streptococcus* strain is non-hemolytic and non-pathogenic.

¶93. The process as described in ¶83, wherein the bulk manufactured hyaluronic acid is isolated from a culture broth of a fermented *Streptococcus* strain.

¶94. The process as described in ¶82, wherein the bulk manufactured hyaluronic acid is substantially free of impurities.

¶95. The process as described in ¶94, wherein the bulk manufactured hyaluronic acid is substantially free of bacterial endotoxin.

¶96. The process as described in ¶95, wherein the level of bacterial endotoxin is <0.25 EU/mL.

¶97. The process as described in ¶94, wherein the bulk manufactured hyaluronic acid is substantially free of bacterial cells.

¶98. The process as described in ¶97, wherein the viable count of bacterial cells is <100 CFU/g.

¶99. The process as described in ¶98, wherein the viable count of bacterial cells is <50 CFU/g.

¶100. The process as described in ¶99, wherein the viable count of bacterial cells is <10 CFU/g.

¶101. The process as described in ¶94, wherein the bulk manufactured hyaluronic acid is substantially free of protein.

¶102. The process as described in ¶101, wherein the level of protein is <1 mg/g.

¶103. The process as described in ¶82, wherein the concentration of the dissolved bulk manufactured biopolymer obtained in step (i) is <0.2%.

¶104. The process as described in ¶103, wherein the concentration of the dissolved bulk manufactured biopolymer obtained in step (i) is 0.10-0.13%.

¶105. The process as described in ¶82, wherein the concentrating is carried out by ultrafiltration.

¶106. The process as described in ¶105, wherein the ultrafiltration is carried out using a ceramic membrane.

¶107. The process as described in ¶82, wherein the desired final concentration in step (iii) is in the range of 0.8 to 3.0% w/v.

¶108. A process as described in ¶107, wherein the desired final concentration is about 1.0% w/v.

¶109. A process as described in ¶107, wherein the desired final concentration is about 1.2% w/v.

¶110. A process as described in ¶107, wherein the desired final concentration is about 2.0% w/v.

¶111. A process as described in ¶82, wherein the desired final concentration in step (iii) is in the range from 0.9 to 1.3% w/v.

¶112. A process as described in ¶82, further comprising aseptic filling of a suitable packaging device with the biopolymer.

¶113. A process as described in ¶112, wherein the packaging device is selected from the group consisting of a syringe, a vial, a catheter and a nebulizer.

¶114. A process as described in ¶82, wherein the formulated hyaluronic acid has a pseudoplasticity index in the range from 500 to 4000.

¶115. A process as described in ¶114, wherein the pseudoplasticity index is in the range from 600 to 1200.

¶116. A process as described in ¶115, wherein the pseudoplasticity index is in the range from 600 to 800.

¶117. A process as described in ¶82, wherein the sterile-filtering is carried out using a membrane of absolute pore size 0.2 micron.

¶118. A process as described in ¶82, wherein all steps are performed under clean room conditions.

¶119. A process as described in ¶82, wherein the bulk manufactured hyaluronic acid is obtained by a process comprising:
(i) precipitating with ethanol a culture broth of a non-hemolytic nonpathogenic hyaluronic acid-producing fermented *Streptococcus* strain;
(ii) dissolving the precipitate obtained in step (i) in sodium chloride/ethanol/charcoal;
(iii) precipitating the dissolved material obtained in step (ii) with cetylpyridinium chloride;
(iv) dissolving the precipitate obtained in step (iii) in sodium chloride/ethanol;
(v) treating the dissolved material obtained in step (iv) with magnesium silicate;
(vi) filtering the treated material obtained in step (v) through a 0.65 micron absolute membrane; and
(vii) precipitating the filtrate obtained in step (vi) with ethanol.

¶120. A formulation of viscoelastic hyaluronic acid suitable for injection during surgery to mammals, obtained by the process as described in ¶82.

¶121. The formulation as described in ¶120, substantially free of impurities and having a pseudoplasticity index greater than 600.

¶122. The formulation as described in ¶121, wherein the hyaluronic acid has an average molecular weight of $3 \times 10^6 \pm 0.6 \times 10^6$ daltons.

¶123. The process as described in ¶121, wherein the hyaluronic acid has an average molecular weight in the range from $2.8 \times 10^6$ to $3.2 \times 10^6$ daltons.

¶124. The formulation as described in ¶120, further comprising a drug.

¶125. The formulation as described in ¶120, wherein the hyaluronic acid is chemically cross-linked.

¶126. The formulation as described in ¶120, wherein the hyaluronic acid is complexed with a metal.

¶126. The formulation as described in ¶120, further comprising a microalgal polysaccharide.

¶127. The formulation as described in ¶126, wherein the microalgal polysaccharide is a polysaccharide isolated from a *Porphyridium* microalga.

¶127. The process as described in any of ¶1, ¶41 or ¶82, wherein the resulting viscoelastic biopolymer is stable and sterile for at least about one year.

¶128. The process of claim 120, wherein the resulting viscoelastic biopolymer is stable and sterile for at least about two years.

¶129. The process of claim 120, wherein the resulting viscoelastic biopolymer is stable and sterile for at least about five years.

¶130. The process as described in any of ¶1, ¶41 or ¶82, wherein no preservative of the viscoelastic biopolymer is used.

¶131. The process as described in any of ¶1, ¶41 or ¶82, further comprising including a microalgal polysaccharide in the formulation.

¶132. The process as described in ¶131, wherein the microalgal polysaccharide is a polysaccharide isolated from a *Porphyridium* microalga.

All publications, patent applications, patents and other references mentioned herein are incorporated by reference in their entirety.

What is claimed is:

1. An industrial process for formulating hyaluronic acid, the process consisting essentially of:
(i) dissolving bulk-manufactured hyaluronic acid having a high average molecular weight of 3.0±0.6 megadaltons in an aqueous medium to form a dilute hyaluronic acid solution having a concentration suitable for sterile-filtering;

(ii) sterile-filtering the dilute hyaluronic acid solution by passage through a membrane suitable for sterile filtration at a minimum flow rate of 750 ml/minute and a pressure of 10 to 15 psi, wherein the pressure does not adversely affect the high average molecular weight of the hyaluronic acid, whereby the sterile-filtering retains the high average molecular weight structure of the hyaluronic acid in the dilute hyaluronic acid solution; and (iii) subsequently concentrating the sterile-filtered hyaluronic acid by ultrafiltration with a membrane having a pore size of 0.002 to 0.1 microns under aseptic conditions to form a sterile solution formulation of a desired final concentration;

wherein the formulation is suitable for medicinal use by injection into a human without further purification following step (iii);

wherein the concentrated hyaluronic acid in the sterile solution formulation has a high average molecular weight of 3.0±0.6 megadaltons; and wherein the concentration of the hyaluronic acid in step (i) is 0.10-0.13% w/v.

2. The process according to claim 1, wherein the hyaluronic acid has an average molecular weight in the range from $2.8 \times 10^6$ to $3.2 \times 10^6$ daltons.

3. The process according to claim 1, further comprising obtaining the bulk manufactured hyaluronic acid for step (i) by isolation of the hyaluronic acid from a culture broth of a fermented *Streptococcus* strain.

4. The process according to claim 3, wherein the *Streptococcus* is a *Streptococcus* species selected from the group consisting of *Streptococcus equi, Streptococcus pyogenes, Streptococcus equisimilis, Streptococcus dysgalactiae* and *Streptococcus zooepidemicus* or another *Streptococcus* strain that is non-hemolytic and non-pathogenic.

5. The process according to claim 1, wherein the bulk manufactured hyaluronic acid is substantially free of impurities.

6. The process according to claim 1, wherein the sterile-filtering is carried out using a membrane of absolute pore size 0.2 micron.

7. The process according to claim 1, wherein the concentrating is carried out by ultrafiltration using a ceramic membrane.

8. The process according to claim 1, wherein the desired final concentration in step (iii) is in the range from 0.8 to 3.0% w/v.

9. The process according to claim 8, wherein the desired final concentration in step (iii) is about 1.0% w/v.

10. The process according to claim 8, wherein the desired final concentration in step (iii) is about 1.2% w/v.

11. The process according to claim 8, wherein the desired final concentration in step (iii) is about 2.0% w/v.

12. The process according to claim 8, wherein the desired final concentration in step (iii) is in the range from 0.9 to 1.3% w/v.

13. The process according to claim 1, further comprising aseptically filling a suitable packaging device with the hyaluronic acid solution formulation obtained in step (iii).

14. The process according to claim 13, wherein the packaging device is selected from the group consisting of a syringe, a vial, a catheter and a nebulizer.

15. The process according to claim 1, wherein the formulated hyaluronic acid has a pseudoplasticity index in the range from 500 to 4000.

16. The process according to claim 1, wherein the membrane suitable for sterile filtration has a pore size of 0.05 to 0.2 microns.

17. The process according to of claim 1, wherein the ultrafiltration is carried out with a membrane having a pore size of about 50 nm.

18. The process according to of claim 1, wherein all steps are performed under clean room conditions.

19. The process according to of claim 1, wherein the hyaluronic acid is not subjected to freeze drying at any stage of bulk manufacturing or formulation.

* * * * *

UNITED STATES PATENT AND TRADEMARK OFFICE
CERTIFICATE OF CORRECTION

PATENT NO. : 9,896,518 B2  
APPLICATION NO. : 14/023196  
DATED : February 20, 2018  
INVENTOR(S) : Menakem Fuchs, Dror Eyal and Yehuda Zelig Page 1 of 1

It is certified that error appears in the above-identified patent and that said Letters Patent is hereby corrected as shown below:

On the Title Page

Item [56], Column 2, Line 1: delete "Reacion"," and insert -- Reaction", --.

Item [74], after "Fish & Richardson", insert -- P.C. --.

In the Claims

Column 20, Line 32: Claim 17, delete "to of" and insert -- to --.

Column 20, Line 35: Claim 18, delete "to of" and insert -- to --.

Column 20, Line 37: Claim 19, delete "to of" and insert -- to --.

Signed and Sealed this  
Eighth Day of May, 2018

Andrei Iancu  
*Director of the United States Patent and Trademark Office*